United States Patent
Park

(10) Patent No.: US 11,534,361 B2
(45) Date of Patent: Dec. 27, 2022

(54) EYESIGHT TRAINING DEVICE FOR COGNITION CORRECTION

(71) Applicant: EDENLUX CORPORATION, Changwon-si (KR)

(72) Inventor: Sungyong Park, Busan (KR)

(73) Assignee: EDENLUX CORPORATION

( * ) Notice: Subject to any disclaimer, the term of this patent is extended or adjusted under 35 U.S.C. 154(b) by 870 days.

(21) Appl. No.: 16/435,879

(22) Filed: Jun. 10, 2019

(65) Prior Publication Data

US 2019/0290530 A1 Sep. 26, 2019

Related U.S. Application Data

(63) Continuation of application No. PCT/KR2016/014736, filed on Dec. 15, 2016.

(51) Int. Cl.
*A61H 5/00* (2006.01)
*A61F 9/00* (2006.01)
(Continued)

(52) U.S. Cl.
CPC .............. *A61H 5/005* (2013.01); *A61B 3/022* (2013.01); *A61F 9/00* (2013.01); *A61F 9/02* (2013.01); *A61H 5/00* (2013.01); *G02B 27/01* (2013.01); *A61H 2201/0157* (2013.01); *A61H 2201/123* (2013.01); *A61H 2201/1215* (2013.01);
(Continued)

(58) Field of Classification Search
CPC .. A61H 5/005; A61H 5/00; A61H 2201/0157; A61H 2201/1215; A61H 2201/123; A61H 2201/1604; A61H 2201/165; A61H 2201/50; A61H 2201/5035; A61H 2201/5043;
(Continued)

(56) References Cited

U.S. PATENT DOCUMENTS 4,896,959 A * 1/1990 O'Brien ................. A61B 3/032
351/203
6,213,956 B1 4/2001 Lawton
(Continued)

FOREIGN PATENT DOCUMENTS

CN 205649486 U 10/2016
EP 3520762 A1 8/2019
(Continued)

OTHER PUBLICATIONS

International Search Report (PCT/KR2016/014736), WIPO, dated Aug. 21, 2017.
(Continued)

*Primary Examiner* — Aaron F Roane

(57) ABSTRACT

An eyesight training device for cognition correction which includes a display unit; a user input unit; and a controller for controlling the display unit to overlap a recognition restraining image, which restrains a visual recognition of a recognition image, with the recognition image and to gradually change a concentration value of the recognition restraining image, and for storing, as recognition level information, information corresponding to a concentration value of the recognition restraining image as of a time when a visibility change confirmation input is input through the user input unit of the visibility change confirmation input is input.

9 Claims, 6 Drawing Sheets

(51) Int. Cl.
*G02B 27/01* (2006.01)
*A61B 3/02* (2006.01)
*A61F 9/02* (2006.01)

(52) U.S. Cl.
CPC ............... *A61H 2201/1604* (2013.01); *A61H 2201/165* (2013.01); *A61H 2201/50* (2013.01); *A61H 2201/5035* (2013.01); *A61H 2201/5043* (2013.01); *A61H 2205/022* (2013.01); *A61H 2205/024* (2013.01)

(58) Field of Classification Search
CPC ........ A61H 2205/022; A61H 2205/024; A61B 3/022; A61F 9/00; A61F 9/02; G02B 27/01
USPC ......................................................... 351/203
See application file for complete search history.

(56) References Cited

U.S. PATENT DOCUMENTS

| | | | |
|---|---|---|---|
| 6,475,162 B1 | 11/2002 | Hu | |
| 7,004,912 B2 | 2/2006 | Polat | |
| 8,066,372 B2 | 11/2011 | Cooperstock et al. | |
| 8,807,749 B2 * | 8/2014 | Fateh | A61B 3/08 351/205 |
| 2001/0050754 A1 | 12/2001 | Hay et al. | |
| 2003/0147048 A1 | 8/2003 | Mihashi | |
| 2003/0214630 A1 * | 11/2003 | Winterbotham | A61H 5/00 351/203 |
| 2005/0041208 A1 | 2/2005 | Winterbotham | |
| 2010/0073469 A1 | 3/2010 | Fateh | |
| 2013/0169929 A1 | 7/2013 | Fateh | |
| 2017/0296421 A1 * | 10/2017 | Travers | A61H 5/00 |
| 2018/0092796 A1 | 4/2018 | Park | |

FOREIGN PATENT DOCUMENTS

| | | |
|---|---|---|
| JP | 2003-204936 A | 7/2003 |
| JP | 2008-036086 A | 2/2008 |
| JP | 2009-279227 A | 12/2009 |
| JP | 2010-511486 A | 4/2010 |
| JP | 2019-528956 A | 10/2019 |
| KR | 10-2004-0047785 A | 6/2004 |
| KR | 10-2009-0040034 A | 4/2009 |
| KR | 10-2009-0049083 A | 5/2009 |
| KR | 10-2010-0116092 A | 10/2010 |
| KR | 10-1670667 B1 | 11/2016 |
| WO | 2008/070683 A1 | 6/2008 |
| WO | 2016/001902 A1 | 1/2016 |

OTHER PUBLICATIONS

Korean Office Action (KR 10-2019-7013427), KIPO, dated Sep. 8, 2020.
Chinese Office Action (CN 201680091641.X), CNIPA, dated Dec. 29, 2020.
Japan Office Action(JP 2019-552433), JPO, dated May 12, 2020.
Extended European Search Report (EP 13924096.7), EPO, dated Sep. 27, 2019.
Korean Notice of Allowance (KR 10-2019-7013427), KIPO, dated Mar. 11, 2021.

* cited by examiner

EYESIGHT TRAINING DEVICE FOR COGNITION CORRECTION

REFERENCE TO RELATED APPLICATIONS

This is a continuation of International Patent Application PCT/KR2016/014736 filed on Dec. 15, 2016, which designates the United States, the entire contents of which are incorporated herein by reference.

FIELD OF THE INVENTION

The disclosure relates to an eyesight training device for cognition correction.

BACKGROUND OF THE INVENTION

Out of human visual functions, cognitive power means a power to recognize a particular image through the left eye and right eye. Generally, the left eye and the right eye do not have the same cognitive power. One of the left and right eyes that has a weaker cognitive power is called amblyopia and the other one of the same is called non-amblyopia. Due to such difference in the cognitive power between the left and right eyes, the non-amblyopia is used more than the amblyopia, and the amblyopia is used relatively less than the non-amblyopia. If the non-amblyopia is continuously used less, corrected eyesight may be decreased and the non-amblyopia feels easily tired to thereby cause a greater difference in the cognitive power between both eyes.

To solve such problem arising from the difference in the cognitive power, a method of blocking a visual field of the non-amblyopia and recognizing an object only through the amblyopia, the so-called blind method has been conventionally used in general.

However, the effect of the blind method is unsatisfactory since the foregoing method does not consider a user's proprietary cognitive power and causes a user to recognize an object only through the amblyopia. In addition, there is a problem that the cognitive power of the non-amblyopia deteriorates by training since a visual field of the non-amblyopia is blocked.

SUMMARY OF THE INVENTION

An aspect of the disclosure is to provide an eyesight training device for cognition correction for measuring and managing a cognitive power of each eye out of a user's visual functions and a difference in the cognitive power between both eyes.

Another aspect of the disclosure is to provide an eyesight training device for providing an eyesight correction training reflecting a measured cognitive power of a user.

Another aspect of the disclosure is to provide an eyesight training device for cognition correction for providing an eyesight correction training reflecting a measured cognitive power of a user for both eyes.

The foregoing object of the disclosure is achieved by providing an eyesight training device including a display unit; a user input unit; and a controller for controlling the display unit for overlapping a recognition restraining image, which restrains a visual recognition of a recognition image, with the recognition image and for gradually changing a concentration value of the recognition restraining image, and for storing, as recognition level information, a concentration value of the recognition restraining image as of a time when a visibility change confirmation input is input through the user input unit.

According to the embodiment of the disclosure as above, the display unit may include a left display corresponding to the left eye and providing a recognition image and a recognition restraining image for the left eye and a right display corresponding to the right eye and providing a recognition image and a recognition restraining image for the right eye.

The display unit may be a single display apparatus providing the recognition image, a recognition restraining image for the left eye and a recognition restraining image for the right, and the display unit may further include a filter for correlative separation of recognition for providing the recognition image to the left and right eyes through the recognition restraining image for the left and right eyes, thereby performing eyesight training with a simple configuration.

The controller may determine which one of the left and right eyes is an amblyopia by using recognition level information on the left eye and recognition level information on the right eye, sets a concentration section of a recognition restraining image for recognition training of the determined amblyopia, and control the display unit to change the concentration value of the recognition restraining image within the set concentration section, thereby enabling an eyesight training that considers a user's cognitive power.

Also, the foregoing object of the disclosure is achieved by providing an eyesight training device including a display unit; a user input unit; and a controller for controlling the display unit to display a recognition image and to gradually change a concentration value of the displayed recognition image, and for storing, as recognition level information, information corresponding to a concentration value of the recognition image as of a time when a visibility change confirmation input is input through the user input unit if such visibility change confirmation input is input.

As described above, according to the disclosure, a user's cognitive power may be measured and managed. Also, an eyesight correction training tailored to a user that considers a measured cognitive power of a user is provided, and thus a user's cognitive power may be improved more effectively.

DETAILED DESCRIPTION OF THE INVENTION

Hereinafter, an eyesight training device according to an embodiment of the disclosure will be described in more detail with reference to accompanying drawings.

Figure 1:
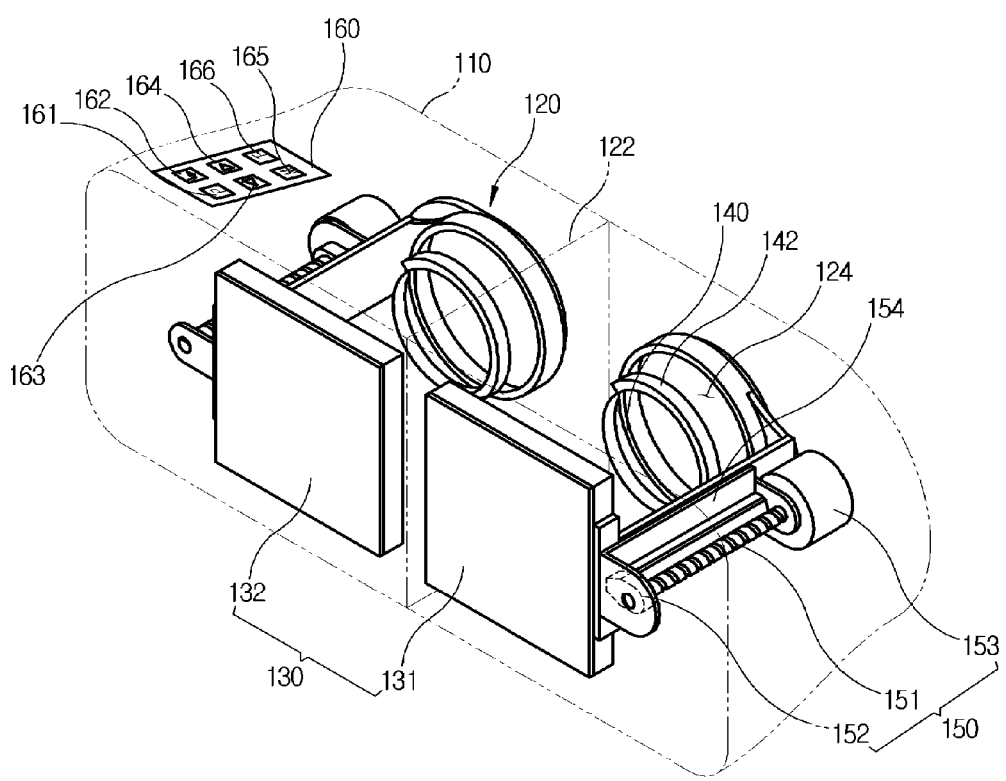
FIG. 1 is a perspective view of an eyesight training device according to an embodiment of the disclosure.

FIG. 1 is a perspective view of an eyesight training device according to an embodiment of the disclosure. The present eyesight training device includes a pair of eyesight training units 120 that are arranged in left and right sides within a housing 110 displayed as an imaginary line. A block panel 122 is installed between the pair of eyesight training units 120 to block visual fields of the left eye and the right eye so that the visual fields of the eyes do not overlap with each other.

The eyesight training units 120 include an eyepiece opening 124 and a display unit 130 that are arranged and face each other in an eyesight direction. The display unit 130 includes a left display 131 corresponding to the left eye and a right display 132 corresponding to the right eye. The left and right displays 131 and 132 display an image thereon for eyesight training, and a user may visually recognize the image displayed by the left and right displays 131 and 132 through the eyepiece openings 124.

On an upper surface of the housing 110, a user input unit 160 is provided to receive a user input from a user. A user inputs a selection of modes such as a measurement mode and a training mode and a user confirmation input through the user input unit 160. In the housing 110, a strap (not shown) or temples of glasses (not shown) may be provided for a user to wear the eyesight training device on his/her head.

The left display 131 of the display unit 130 displays a left-eye recognition image in a front side of the eyesight direction of a user's left eye. The right display 132 displays a right-eye recognition image in a front side of the eyesight direction of a user's right eye. The left-eye image and right-eye image displayed as above may be equal or different from each other. The recognition image displayed as above may include a still image such as a dot, line, landscape image, figure, geometric pattern or character, or video, or 3D image. Also, the image may be a colored image. To provide such image as above, the display unit 130 may include an electronic display apparatus such as liquid crystal display (LCD) and organic light emitting diode (OLED). Otherwise, the display unit 130 may be mounted with an external display apparatus such as a smartphone.

A lens 140 is held by a lens holder 142 and is arranged between the eyepiece opening 124 and the display unit 130. A user recognizes an image provided in a front side of an eyesight direction through the eyepiece opening 124 and the lens 140. The lens 140 may be provided as a convex lens. A convex lens changes a focal length between a user's eyes and an image and causes a user to recognize the image to be at a distance farther than the actual distance to thereby extend a perspective of the image. Such lens may be replaced by mirrors that refract an optical path between the eyes and an image. In such case, mirrors extend a distance of visual field between eyes and an image from the actual distance and extend the perspective of the image. Also, the lens 140 may be provided as a polarizing lens or color lens to separate an image, which is recognized by both eyes, into a left-eye recognition image and a right-eye recognition image, as necessary.

A display mover 150 moves the display unit 130 in forward and backward directions along the eyesight direction of a user. The display mover 150 includes a lead screw 151, a moving body 152 movably coupled to the lead screw 151, and a driving motor 153 rotatably driving the lead screw 151.

The lead screw 151 is rotatably installed in a fixing support 154 provided in the housing 110 and is rotated and driven by the driving motor 153. A rotational motion of the lead screw 151 is converted into a sliding movement of the moving body 152 in forward and backward directions. The moving body 152 is integrally coupled to the display unit 130 so that the display unit 130 may reciprocate in forward and backward directions by the rotational motion of the lead screw 151.

The block panel 122 is installed within the housing 110 and separates an inside part of the housing 110 into two parts corresponding to the left eye and right eye, respectively. By the block panel 122, a user's left eye recognizes only a left-eye recognition image displayed by the left display 131, and a user's right eye recognizes only a right-eye recognition image displayed by the right display 132.

The eyesight training device according to the embodiment of the disclosure described above are provided as two individual display apparatuses, which function as the left display 131 for providing a left-eye recognition image to a user's left eye and the right display 132 for providing a right-eye recognition image to a user's right eye. In the embodiment, the eyesight training device employs two independent display apparatuses, but may perform the same function with a single display apparatus. In such case, the single display apparatus has a screen divided into left and right sides, and displays on the screen a left-eye recognition image and a right-eye recognition image that are spaced from each other. A region of the single display apparatus that displays the left-eye recognition image falls under a left display, and another region of the single display apparatus that displays the right-eye recognition image falls under a right display.

Figure 2:
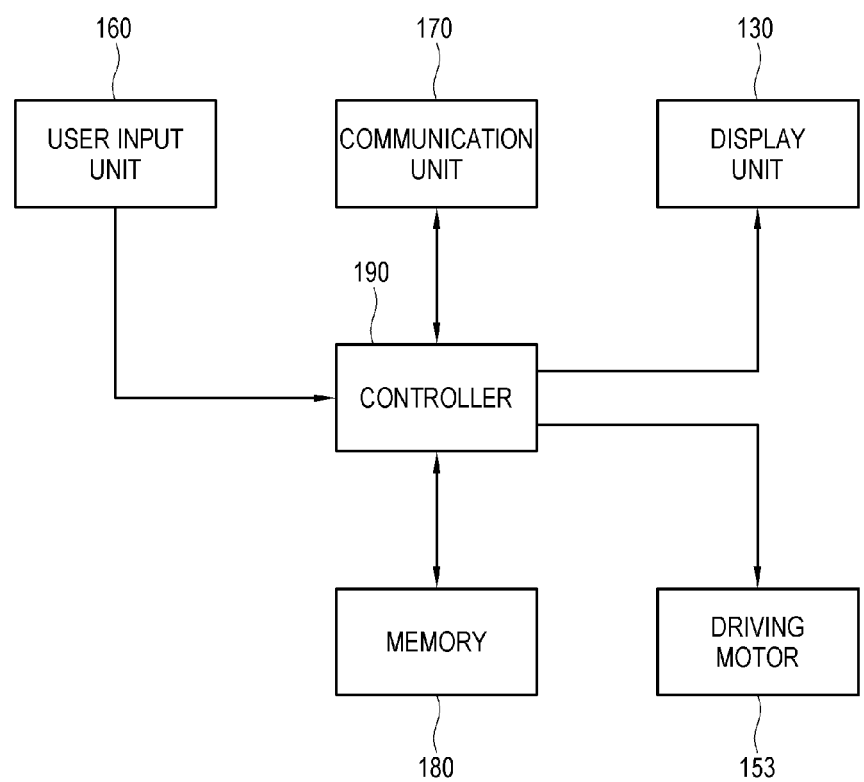
FIG. 2 is a control block diagram of the eyesight training device according to the embodiment of the disclosure.

FIG. 2 is a control block diagram of the eyesight training device according to the disclosure.

The user input unit 160 is provided on an upper surface or a lateral side of the eyesight training device, and through the user input unit 160, a controller 190 receives information or a condition input by a user. The user input unit 160 includes a plurality of user input buttons 161, 162, 163, 164, 165 and 166. The buttons specifically include a power input button 161, a user confirmation button 162, a forward movement button 163, a backward movement button 164, a measurement mode selection button 165 and a training mode selection button 166. A user input which is input through the user input unit 160 is received by the controller 190 and then the controller 190 controls the eyesight training device to perform an operation corresponding to the user input. The user input unit 160 in the form of the buttons may be replaced by a keypad, touch screen, etc. In the embodiment, the user input unit 160 is attached to the eyesight training device, but may be provided as a wired or wireless remote controller or may be replaced by an application of a mobile device such as a smartphone. The user input unit 160 may employ a microphone to recognize voice.

A communication unit 170 communicates with an external device such as a smartphone, tablet PC and a user server in a wired or wireless manner. Through the communication unit 170, the eyesight training device may transmit data to an external device or receive data from an external device.

A memory 180 stores therein user information, recognition level information, training data and various data necessary for operations of the eyesight training device.

The controller 190 controls overall operations of the eyesight training device according to the embodiment of the disclosure. The controller 190 controls the driving motor 153 to control a movement of the display unit 130. The controller 190 may individually control operations of the left display 131 and the right display 132. The controller 190 may control the left display 131 and the right display 132 to display a left-eye recognition image and a right-eye recognition image on the left display 131 and the right display 132, respectively. The controller 190 may control the left display 131 and the right display 132 to overlap a recognition restraining image with a left-eye recognition image and right-eye recognition image. The controller 190 may control the left display 131 and the right display 132 to change a concentration value of the displayed recognition restraining image.

The present eyesight training device may be driven by a battery (not shown) provided therein or may be connected to an external power source and driven thereby.

The eyesight training device according to the embodiment of the disclosure may be used when a user's eyes are not in a corrected state as well as when a user's eyes are in a corrected state. When a user's eyes are not in a corrected state, a user may press the forward movement button 163 and the backward movement button 164 of the user input unit 160 and move the left display 131 and the right display 132 and change the focal length to thereby make his/her eyes corrected without wearing glasses and may have an eyesight training.

Figure 3:
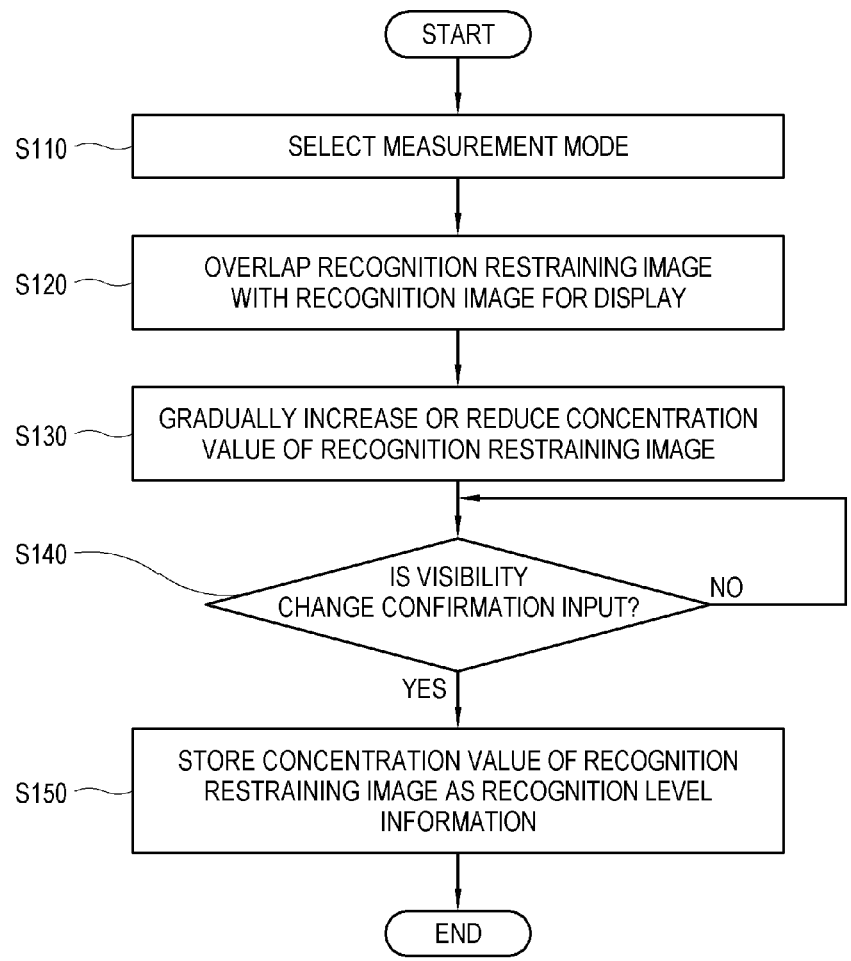
FIG. 3 is a flowchart showing an example of operations of a measurement mode using the eyesight training device according to the embodiment of the disclosure.
Figure 4:
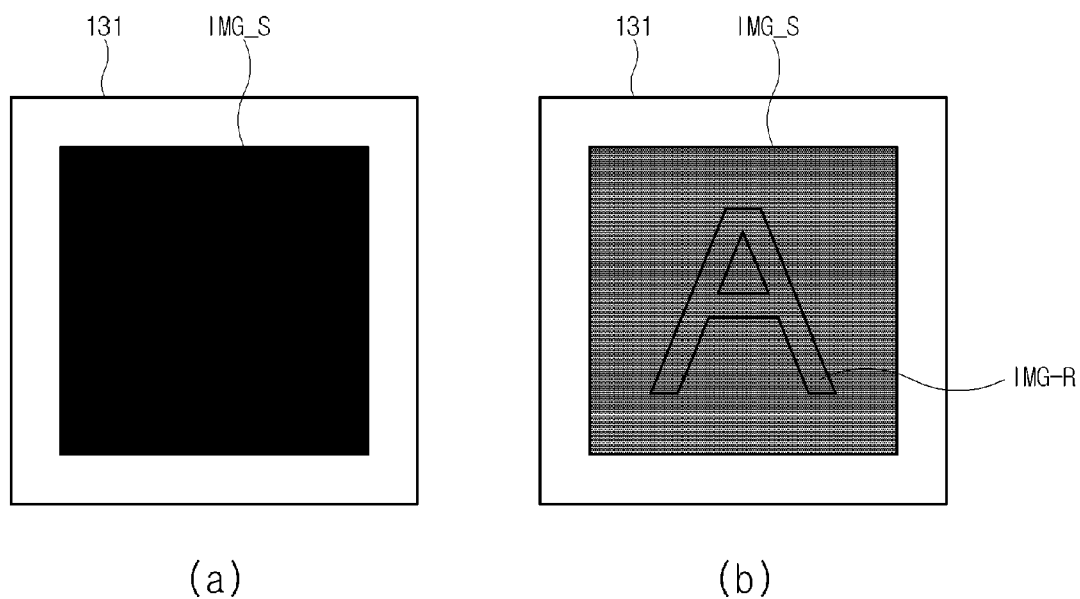
FIG. 4 is a reference view for explaining the measurement mode in FIG. 3.

FIG. 3 is a flowchart showing an example of operations of a measurement mode using the eyesight training device according to the embodiment of the disclosure. FIG. 4 is a reference view for explaining the measurement mode in FIG. 3.

Hereinafter, operations of the measurement mode using the eyesight training device according to the embodiment of the disclosure will be described with reference to FIGS. 3 and 4. The measurement mode is separately performed with respect to a user's left eye and right eye. When the measurement mode is performed with respect to the left eye, the controller 190 turns off power supplied to the right display 132 and blocks a visual field of a user's right eye. Conversely, when the measurement mode is performed with respect to the right eye, the controller 190 turns off power supplied to the left display 131 and blocks a visual field of a user's left eye. Measurement may be performed in the order set by a user's manipulation or set in advance by the controller 190. Hereinafter, a performance of the measurement mode with respect to the left eye will be described as an example.

First, a user presses the power input button 161 of the user input unit 160 to apply power to the eyesight training device. A user wears the eyesight training device and then presses the measurement mode selection button 165 of the user input unit 160 to select the measurement mode (S110).

If the measurement mode is selected, the controller 190 displays a left-eye recognition image IMG_R on the left display 131 and overlaps a recognition restraining image IMG_S with the left-eye recognition image IMG_R while the power of the right display 132 is turned off (S120). The overlapped recognition restraining image IMG_S may be set to have an initial concentration value, which is 100% to fully block the recognition of the recognition image IMG_R or is 0% to fully allow the recognition of the recognition image IMG_R. (a) in FIG. 4 shows an image displayed by the left display 131 when the concentration value of the recognition restraining image IMG_S is 100%.

Thereafter, the controller 190 controls the left display 131 to gradually change the concentration value of the recognition restraining image IMG_S (S130). For example, the controller 190 controls the left display 131 to reduce the concentration value of the recognition restraining image IMG_S, which is 100%, at a preset interval, e.g., at an interval of 1%. Otherwise, the controller 190 controls the left display 131 to consecutively reduce the concentration value of the recognition restraining image IMG_S.

The controller 190 confirms whether a visibility change confirmation input is input through the user input unit 160 while the concentration value of the recognition restraining image IMG_S is being changed (S140).

The visibility change confirmation input is input by a user by pressing the user confirmation button 162 of the user input unit 160 at a time when a user recognizes the recognition image IMG_R in the state where the concentration value of the recognition restraining image IMG_S is being changed. (b) in FIG. 4 shows an example of a screen displayed by the left display 131 at the time when the visibility is changed. The time when visibility is changed means the time when the recognition image IMG_R is recognized in case the concentration value of the recognition restraining image IMG_S is gradually reduced, and means the time when the recognition image IMG_R is not recognized in case the concentration value of the recognition restraining image IMG_S gradually increases from 0%. However, it is more accurate to confirm the time of change in visibility by gradually reducing the concentration value of the recognition restraining image IMG_S from 100%.

If the visibility change confirmation input is input through the user input unit 160, the controller 190 stores, as recognition level information, information falling under the concentration value of the recognition restraining image IMG_S as of such time (S150).

Figure 5:
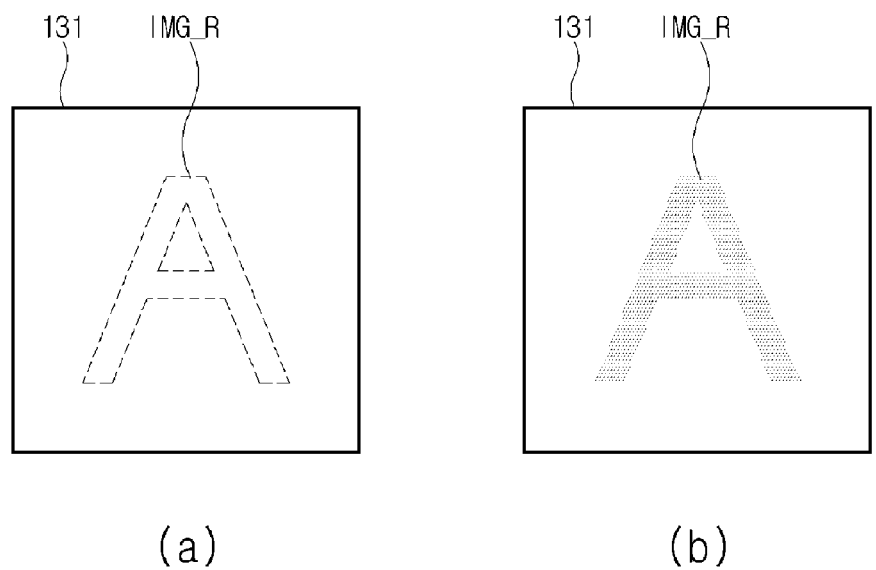
FIG. 5 is a reference view for explaining another embodiment of the measurement mode in FIG. 3.

FIG. 5 is a reference view for explaining another embodiment of the measurement mode in FIG. 3. For clarity, the same portion as the operation of the foregoing measurement mode will not be described.

Referring to FIG. 5, the measurement mode may be performed by adjusting the concentration value of the recognition image IMG_R rather than adjusting the concentration value of the recognition restraining image.

(a) in FIG. 5 shows the recognition image IMG_R which is displayed with a concentration value of 0% by the left display 131. In such case, the recognition restraining image is in a white background and the recognition image IMG_R is also in white and thus a user does not recognize the recognition image IMG_R.

Thereafter, the controller 190 controls the concentration value of the recognition image IMG_R to be gradually increased so that the recognition image is gradually changed from white to grey. As shown in (b) in FIG. 5, a user may recognize the recognition image IMG_R that he/she did not recognize before. In such case, a user inputs a visibility change confirmation input through the user confirmation button 162 of the user input unit 160. The controller 190 stores, as recognition level information, the concentration value of the recognition image IMG_R as of the time when the visibility change confirmation input is input.

In the case of the measurement mode in FIG. 5, it is desirable to gradually increase the concentration value of the recognition image for measurement so that a user may obtain more accurate recognition information.

The foregoing measurement mode may be performed in the same manner with respect to a user's right eye.

In accordance with the performance of the measurement mode, the eyesight training device according to the embodiment of the disclosure may measure and confirm a user's proprietary recognition level information. Such recognition level information is an element relating to the cognitive power out of a user's visual functions and may be used as an important parameter to evaluate a user's eyesight. Such measurement mode may be also used to identify a user's eyesight characteristic and to provide eyesight training tailed to a user by taking into account the identified eyesight characteristic, thereby maximizing the effect of improvement of a user's eyesight.

The eyesight training device according to the embodiment of the disclosure shown in FIG. 1 separately provides a left-eye recognition image and a right-eye recognition image for a user's left eye and right eye, respectively, through the two separate display apparatuses. The eyesight training device may be used as a mounting-type device that may be mounted on a user's head for usage.

The present eyesight training device may employ a single display apparatus. If the eyesight training device is implemented as a single display apparatus, it may include a filter for separation of recognition. Such filter for separation of recognition enables a user to separately recognize a recognition image displayed by the single display apparatus, through a user's left and right eyes.

For example, if a filter for separation of recognition is implemented as a red/green filter and a red filter is provided for a user's left eye and a green filter is provided for a user's right eye, the controller 190 may control the single display apparatus to separately display red and green of a recognition restraining image. In such case, a user's left eye recognizes the recognition image only through the recognition restraining image displayed in red, and a user's right recognizes the recognition image only through the recognition restraining image displayed in green.

If the foregoing eyesight training device is implemented as a single display, the eyesight training device may be implemented as a simple configuration such as a display of a smartphone, buttons and a red/green filter. Accordingly, the eyesight training device with such simple configuration may measure a user's recognition level information and perform the training mode based on the measured recognition level information without being affected by time or place.

Figure 6:
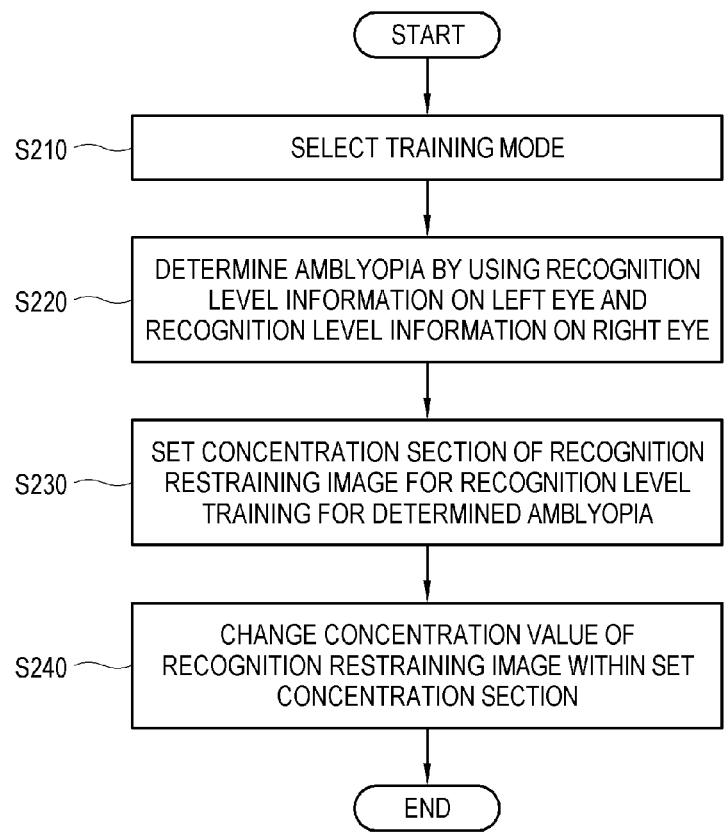
FIG. 6 is a flowchart showing an example of operations of a training mode using an eyesight training device according to the disclosure.

FIG. 6 is a flowchart showing an example of operations of a training mode using the eyesight training device according to the disclosure.

A user applies power to the eyesight training device by pressing the power input button 161 of the user input unit 160. Thereafter, a user wears the eyesight training device on his/her head and presses the training mode selection button 166 of the user input 160 and selects the training mode (S210).

If the training mode is selected, the controller 190 determines which one of left and right eyes is amblyopia by using the stored recognition level information on the left and right eyes (S220). The amblyopia is determined by using the recognition level information on the left and right eyes that has been stored in the measured mode, and one of the left and right eyes for which the concentration value of the recognition restraining image is lower is determined as the amblyopia. For example, if the concentration value of the recognition restraining image of the left eye is 75% and that of the right eye is 60% as of the time when the visibility change confirmation input is input in the measurement mode, a user's right eye is determined to be the amblyopia.

If the amblyopia is determined, the controller 190 sets a concentration section of the recognition restraining image for recognition level training of the determined amblyopia (S230). Since the right eye is the amblyopia in the foregoing example, the controller 190 sets a concentration section of the recognition restraining image for the right eye. The concentration section may be set to be in a predetermined rage, e.g., in a range of 55 to 65% based on 60% as the concentration value of the recognition restraining image determined in the measurement mode. Such range may be set automatically by the controller, or by a user.

If the concentration section is set, the controller 190 changes the concentration value of the recognition restraining image within the set concentration section (S240). That is, the controller 190 controls the right display 132 to gradually change the concentration value of the recognition restraining image displayed by the right display 132.

It is desirable for the controller 190 to change the concentration value of the recognition restraining image displayed by the left display 131 and to make the left eye, which is non-amblyopia, clearly recognize the recognition image. The purpose of the foregoing is to secure a visual field of the left eye as the non-amblyopia and to prevent the cognitive power of the left eye from being deteriorated during the training process of the right eye as the amblyopia.

The foregoing training mode as shown in FIG. 5 may be performed through the same operations as the training mode in FIG. 6 except for changing the concentration value of the recognition image within the set range rather than changing the concentration value of the recognition restraining image in case a user's recognition level information is measured by changing the concentration value of the recognition image in the measurement mode.

Through the foregoing training mode, a user's amblyopia is alternately changed between the cognitive and non-cognitive states of the recognition image, thereby improving the cognitive power of a user and correcting the difference in the cognitive power between the left and right eyes.

In the foregoing training mode, the recognition image is displayed for a user's both eyes and the concentration value of the recognition restraining image is changed to change the recognition level of one recognition image. However, the training mode may be also performed by blocking the visual field of the non-amblyopia and change the concentration value of the recognition restraining image only for the amblyopia. In such case, the controller 190 may turn off power supplied to the display corresponding to the non-amblyopia to block the visual field of the non-amblyopia.

What is claimed is:

1. An eyesight training device comprising:
a display unit;
a user input unit; and
a controller for controlling the display unit for overlapping a recognition restraining image, which restrains a visual recognition of a recognition image, with the recognition image and for gradually changing a concentration value of the recognition restraining image, and for storing, as recognition level information, information corresponding to a concentration value of the recognition restraining image as of a time when a visibility change confirmation input is input through the user input unit if the visibility change confirmation input is input.

2. The eyesight training device according to claim 1, wherein the controller stores recognition level information on a user's left eye and recognition level information on a user's right eye, respectively.

3. The eyesight training device according to claim 2, wherein the display unit comprises a left display corresponding to the left eye and providing a recognition image and a recognition restraining image for the left eye and a right display corresponding to the right eye and providing a recognition image and a recognition restraining image for the right eye.

4. The eyesight training device according to claim 2, wherein the display unit is a single display apparatus providing the recognition image, the recognition restraining image for the left eye, and the recognition restraining image for the right eye, and further comprises a correlative filter for separation of recognition for providing the recognition image to the left and right eyes through the recognition restraining images for the left and right eyes.

5. The eyesight training device according to claim 3, wherein the controller determines which one of the left and right eyes is an amblyopia by using recognition level information on the left eye and recognition level information on the right eye, sets a concentration section of a recognition restraining image for recognition level training of the determined amblyopia, and controls the display unit to change the concentration value of the recognition restraining image within the set concentration section.

6. The eyesight training device according to claim 4, wherein the controller determines which one of the left and right eyes is an amblyopia by using recognition level information on the left eye and recognition level information on the right eye, sets a concentration section of a recognition restraining image for recognition level training of the determined amblyopia, and controls the display unit to change the concentration value of the recognition restraining image within the set concentration section.

7. The eyesight training device according to claim 1, wherein the controller sets a concentration section of a recognition restraining image for the recognition level training by using the recognition level information and controls the display unit to change a concentration value of the recognition restraining image within the set concentration section.

8. An eyesight training device comprising:
a display unit;
a user input unit; and
a controller for controlling the display unit to display a recognition image and to gradually change a concentration value of the displayed recognition image, and for storing, as recognition level information, information corresponding to a concentration value of the recognition image as of a time when a visibility change confirmation input is input through the user input unit if the visibility change confirmation input is input.

9. The eyesight training device according to claim 8, wherein the controller sets a concentration section of a recognition image for recognition level training by using the recognition level information, and controls the display unit to change a concentration value of the recognition image within the set concentration section.

* * * * *